United States Patent
Zhang et al.

(10) Patent No.: US 11,271,237 B2
(45) Date of Patent: Mar. 8, 2022

(54) ORGANIC REDOX MOLECULES FOR FLOW BATTERIES

(71) Applicant: UCHICAGO ARGONNE, LLC, Chicago, IL (US)

(72) Inventors: Lu Zhang, Lisle, IL (US); Jingjing Zhang, Downers Grove, IL (US); Ilya A. Shkrob, Chicago, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 23 days.

(21) Appl. No.: 16/524,666

(22) Filed: Jul. 29, 2019

(65) Prior Publication Data

US 2021/0036355 A1    Feb. 4, 2021

(51) Int. Cl.
| | |
|---|---|
| *H01M 8/18* | (2006.01) |
| *H01M 2/16* | (2006.01) |
| *H01M 50/46* | (2021.01) |
| *H01M 50/411* | (2021.01) |
| *C07D 211/94* | (2006.01) |

(52) U.S. Cl.
CPC ......... *H01M 8/188* (2013.01); *H01M 50/411* (2021.01); *H01M 50/46* (2021.01); *C07D 211/94* (2013.01)

(58) Field of Classification Search
CPC ..... H01M 8/188; H01M 50/46; H01M 50/411
See application file for complete search history.

(56) References Cited

U.S. PATENT DOCUMENTS

| | | | |
|---|---|---|---|
| 3,996,064 | A | 12/1976 | Thaller |
| 4,362,791 | A | 12/1982 | Kaneko et al. |
| 5,366,824 | A | 11/1994 | Nozaki |
| 5,708,123 | A | 1/1998 | Johannsen et al. |
| 5,709,968 | A | 1/1998 | Shimizu |
| 6,692,862 | B1 | 2/2004 | Zocchi |

(Continued)

FOREIGN PATENT DOCUMENTS

| | | |
|---|---|---|
| EP | 2001091434 A1 | 4/2001 |
| JP | 2000235867 * | 8/2000 |

(Continued)

OTHER PUBLICATIONS

Baran, et al., Designing Redox-Active Oligomers for Crossover-Free, Non-aqueous Redox-Flow Batteries with High Volumetric Energy Density, Chemistry of Materials, pp. 3861-3866 (Year: 2018).*

(Continued)

*Primary Examiner* — Jayne L Mershon
(74) *Attorney, Agent, or Firm* — Olson & Cepuritis, Ltd.

(57) ABSTRACT

The present invention provides a redox flow battery comprising a negative electrode (also referred to herein as an "anode") immersed in a first liquid electrolyte (also referred to herein as a "negative electrolyte" or "anolyte"), a positive electrode (also referred to herein as a "cathode") immersed in a second liquid electrolyte (also referred to herein as a "positive electrolyte" or "catholyte"), and a cation-permeable separator (e.g., a membrane or other cation-permeable material) partitioning the negative electrode/anolyte from the positive electrode/catholyte. The redox reactant of the catholyte comprises a compound of Formula (I) as described herein.

12 Claims, 6 Drawing Sheets

(56) References Cited

U.S. PATENT DOCUMENTS

| | | | |
|---|---|---|---|
| 6,872,376 | B2 | 3/2005 | Tanaka et al. |
| 7,258,947 | B2 | 8/2007 | Kubata et al. |
| 7,320,844 | B2 | 1/2008 | Skyllas-Kazacos |
| 8,003,260 | B2 | 8/2011 | Exnar et al. |
| 8,968,885 | B2 | 3/2015 | Brown et al. |
| 9,300,000 | B2 | 3/2016 | Skyllas-Kazacos |
| 9,966,625 | B2 | 5/2018 | Zhang et al. |
| 2004/0191635 | A1 | 9/2004 | Otsuki et al. |
| 2006/0199080 | A1 | 9/2006 | Amine et al. |
| 2006/0263695 | A1 | 11/2006 | Dahn et al. |
| 2007/0092802 | A1 | 4/2007 | Ahn et al. |
| 2008/0220335 | A1 | 9/2008 | Casteel |
| 2008/0241643 | A1 | 10/2008 | Lepp et al. |
| 2009/0017379 | A1 | 1/2009 | Inatomi et al. |
| 2009/0176162 | A1 | 7/2009 | Exnar et al. |
| 2010/0047671 | A1 | 2/2010 | Chiang et al. |
| 2010/0081059 | A1 | 4/2010 | Exnar et al. |
| 2010/0151356 | A1 | 6/2010 | Watt et al. |
| 2010/0237298 | A1 | 9/2010 | Armand et al. |
| 2010/0297481 | A1 | 11/2010 | Son et al. |
| 2010/0323264 | A1 | 12/2010 | Chiang et al. |
| 2011/0052945 | A1 | 3/2011 | Whitacre |
| 2011/0189549 | A1 | 8/2011 | Sun et al. |
| 2011/0195283 | A1 | 8/2011 | Sun et al. |
| 2011/0200848 | A1 | 8/2011 | Chiang et al. |
| 2011/0294003 | A1 | 12/2011 | Zhang et al. |
| 2011/0294017 | A1 | 12/2011 | Weng et al. |
| 2012/0135278 | A1 | 5/2012 | Yoshie et al. |
| 2013/0189571 | A1 | 7/2013 | Abouimrane et al. |
| 2015/0191470 | A1 | 7/2015 | Fahrenbach et al. |
| 2015/0372333 | A1 | 12/2015 | Odom et al. |
| 2015/0380760 | A1 | 12/2015 | Spaziante et al. |
| 2016/0013506 | A1 | 1/2016 | Dong |
| 2018/0072669 | A1 | 3/2018 | Liu et al. |
| 2018/0331363 | A1* | 11/2018 | Winsberg ............... H01M 4/38 |

FOREIGN PATENT DOCUMENTS

| | | | |
|---|---|---|---|
| WO | 200129920 | A1 | 4/2001 |
| WO | 2011131959 | A1 | 10/2011 |

OTHER PUBLICATIONS

Abraham, K.M. et al., n-Butylferrocene for Overcharge Protection of Secondary Lithium Batteries, Journal of the Electrochemical Society, 137 (6), 1856-1857 (1990).

Amine, K., Develop and Evaluate Materials and Additives That Enhance Thermal and Overcharge Abuse, Department of Energy, (Argonne National Laboratory), Advanced Battery Research Review, Washington, D.C. (2010).

Armand, M. et al., Conjugated Dicarboxylate Anodes for Li-ion Batteries, Nature Materials, 8 (2), 120-125 (2009).

Behl, W. K. et al., Electrochemical Overcharge Protection of Rechargeable Lithium Batteries, I. Kinetics of Iodide/Tri-Iodide/Iodine Redox Reactions on Platinum LiAsF6/Tetrahydrofuran Solutions, Journal of the Electrochemical Society, 135 (1), 16-21 (1988).

Behl, W. K. et al., Electrochemical Overcharge Protection of Rechargeable Lithium Batteries, II. Effect of Lithium Iodide-Iodine Additives on the Behavior of Lithium Electrode in LiAsF6-Tetrahydrofuran Solutions, Journal of the Electrochemical Society, 135 (1), 21-25 (1988).

Brushett, F.R. et al., An All-Organic Non-Aqueous Lithium-Ion Redox Flow Battery, Advanced Energy Materials, 1-7, (2012).

Buhrmester, C. et al., Studies of Aromatic Redox Shuttle Additives for LiFePO4-Based Li-Ion Cells, Journal of the Electrochemical Society, 152 (12) A2390-A2399 (2005).

Chakrabarti, M.H. et al., Evaluation of Electrolytes for Redox Flow Battery Applications, Electrochimica Acta, 52(5), 2189-2195 (2007).

Chang, D.W. et al., Novel Quinoxaline-Based Organic Sensitizers for Dye-Sensitized Solar Cells, Organic Letters 13(15), 3880-3883 (2011).

Chen, Z. et al., Redox Shuttles for Safer Lithium-Ion Batteries, Electrochimica Acta, 54 (24), 5605-5613 (2009).

Chen, Z. et al., Lithium Borate Cluster Salts as Redox Shuttles for Overcharge Protection of Lithium-Ion Cells, Electrochemical and Solid State Letters, 13 (4), A39-A42 (2010).

Crabtree, G. et al., Integrating Renewable Electricity on the Grid—A Report by the APS Panel on Public Affairs, American Physical Society, Washington, D.C. (2010).

Ding, Y. et al., Molecular Engineering of Organic Electroactive Materials For Redox Flow Batteries, Chem. Soc. Rev. 47, 69-103 (2018).

Dudata, M. et al., Semi-Solid Lithium Rechargeable Flow Battery, Advanced Energy Materials, 1 (4) 511-516 (2011).

Eyer, J. et al., Energy Storage for the Electricity Grid: Benefits and Market Potential Assessment Guide, A Study for the DOE Energy Storage Systems Program, Sandia National Laboratories (2010).

Hu, B. et al., A Long Cycling Aqueous Organic Redox Flow Battery (AORFB) Towards Sustainable and Safe Energy Storage, Journal of the American Chemical Society, http://pubs.acs.org. Dec. 15, 2016 (pp. 1-10).

Huskinson, B. et al., A Metal-Free Organic-Inorganic Aqueous Flow Battery, Nature 12909, vol. 505, 195-210, (2014).

Janoschka, T. et al., Aqueous Redox-Flow Battery With High Capacity and Power: The TEMPTMA/MV System, Angew. Communications Int. Ed 55, 1-5 (2016).

Kim, J.H. et al., Development of Metal-Based Electrodes for Non-aqueous Redox Flow Batteries, Electrochemistry Communication, 13 (9) 997-1000 (2011).

Lee, J.-Y et al., Low Band-Gap Polymers Based on Quinoxaline Derivatives and Fused Thiophene as Donor Materials for High Efficiency Bulk-Heterojunction Photovoltaic Cells, Journal of Materials Chemistry 19 (28), 4938-4945 (2009).

Leung, P. et al., Recent Developments In Organic Redox Flow Batteries: A Critical Review, Journal of Power Sources 360, 243-283 (2017).

Li, Zhen et al., Electrochemical Properties of an All-Organic Redox Flow Battery Using 2,2,6,6-Tetramethyl-1-Piperidinyloxy and N-Methylphthalimide, Electrochemical and Solid State Letters 14 (12), A171-A173 (2011).

Lin, K. et al., Alkaline Quinone Flow Battery, Science, vol. 349 (6255), 1529-1532 (2015).

Lin, K., A Redox-Flow Battery With An Alloxazine-Based Organic Electrolyte, Nature Energy 10.1038, vol. 1, 1-8 (2016).

Liu, J. et al., TEMPO and Its Derivatives in Organic Redox-Flow Batteries, Univ. Chem. 32 (11), 32-44 (2017).

Liu, T. et al., A Total Organic Aqueous Redox Flow Battery Employing a Low Cost and Sustainable Methyl Viologen Anolyte and 4-HO-TEMPO Catholyte, Advanced Energy Materials 6, 1-8 (2016).

Liu, Q. et al., Non-aqueous Chromium Acetylacetonate Electrolyte for Redox Flow Batteries, Electrochemistry Communications, 12 (11), 1634-1637 (2010).

Liu, Q. et al., Non-aqueous Vanadium Acetylacetonate Electrolyte for Redox Flow Batteries, Electrochemistry Communications, 11, 2312-2315 (2009).

Matsuda, Y. et al., A Rechargeable Redox Battery Utilizing Ruthenium Complexes with Non-Aqueous Organic Electrolyte, Journal of Applied Electrochemistry, 18 (6), 909-914 (1988).

Matsunaga, T. et al., High-Performance Lithium Secondary Batteries Using Cathode Active Materials of Triquinoxalinylenes Exhibiting Six Electron Migration; Chemistry Letters 40 (7), 750-752 (2011).

Moshurchak, L.M. et al., High-Potential Redox Shuttle for Use in Lithium-Ion Batteries, Journal of the Electrochemical Society, 156 (4) A309-A312 (2009).

Pan, F. et al., Redox Species of Redox Flow Batteries: A Review, Molecules 20, 20499-20517 (2015).

Ponce De Leon, C. et al., Redox Flow Cells for Energy Conversion, Journal of Power Sources, 160 (1), 716-732 (2006).

Sevov, C. et al., Cyclopropenium Salts as Cyclable, High-Potential Catholytes in Nonaqueous Media, Advanced Energy Materials 1602027, 1-5 (2016).

(56) References Cited

OTHER PUBLICATIONS

Skyllas-Kazacos, M. et al., Progress in Flow Battery Research and Development, Journal of the Electrochemical Society, 158 (8), R55-R79 (2011).

Sleightholme, A. E.S. et al., Non-aqueous Manganese Acetylacetonate Electrolyte for Redox Flow Batteries, Journal of Power Sources, 196 (13), 5742-5745 (2011).

Tormena, C.F. et al., Revisiting The Stability of Endolexo Diels-Alder Adducts Between Cyclopentadiene and 1,4-Benzoquinone, Journal Brazil Chemical Society 21 (1), pp. 112-118 (2010).

Walker, W. et al., Ethoxycarbonyl-Based Organic Electrode for Li-Batteries, Journal of the American Chemical Society, 132 (18), 6517-6523 (2010).

Walker, W. et al., Electrochemical Characterization of Lithium 4,4'-tolane-dicarboxylate for Use as a Negative Electrode in Li-Ion Batteries, Journal of Materials Chemistry, 21 (5), 1615-1620 (2011).

Wang, W. et al., A New Redox Flow Battery Using Fe/V Redox Couples in Chloride Supporting Electrolyte, Energy & Environmental Science, 4 (10), 4068-4073 (2011).

Weber, A.Z. et al., Redox Flow Batteries: A Review, Journal of Applied Electrochemistry, 41 (10) 1137-1164 (2011).

Wen, J. et al., A Review on Lithium-Ion Batteries Safety Issues: Existing Problems and Possible Solutions, Materials Express 2, (3), pp. 197-212 (2012).

Winsberg, J. et al., Redox-Flow Batteries: From Metals to Organic Redox-Active Materials, Angew. Chem. Int. Ed. 56, 686-711 (2017).

Yamamura, T. et al., Electrochemical Investigation of Uranium p-diketonates For All-Uranium Redox Flow Battery, Electrochimica Acta 48, 43-50 (2002).

Yang, Z. et al., Electrochemical Energy Storage for Greed Grid. Chemical Reviews, 111 (5), 3577-3613 (2011).

Yates, P. et al., The 1:1 and 2:1 Adducts of Cyclopentadiene with p-Benzoquinone, Can. J. Chemical 68, pp. 1984-1900 (1990).

Zhang, L. et al., Redox Shuttle Additives For Lithium-Ion Battery, Lithium Ion Batteries—New Developments 7, 173-189 (2012).

Zhang, L. et al., Molecular Engineering Towards Safer Lithium-Ion Batteries: A Highly Stable and Compatible Redox Shuttle for Overcharge Protection, Energy & Environmental Science 5, 8204-8207 (2012).

Zhang, L. et al., Redox Shuttles For Overcharge Protection of Lithium-Ion Batteries, ECS Transactions 45 (29), 57-66 (2013).

Zhen, L. et al., Electrochemical Properties of an All-Organic Redox Flow Battery Using 2,2,6,6-Tetramethyl-1-Piperidinyloxy and N-Methylphthalimide, Electrochemical and Solid State Letters, 14 (12), A171-A173 (2011).

* cited by examiner

ORGANIC REDOX MOLECULES FOR FLOW BATTERIES

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to redox flow batteries. More particularly, this invention relates to organic redox materials for use in redox flow batteries.

BACKGROUND OF THE INVENTION

Cost effective, scalable energy storage systems are needed to improve the energy efficiency of the electrical grid (e.g., load-leveling, frequency regulation) and to facilitate the large-scale penetration of renewable energy resources (e.g., wind, solar). While alternative energy technologies exist, they cannot be directly connected to the grid because of their variable output. Electrochemical energy storage may provide the best combination of efficiency, cost, and flexibility to enable these applications. Of particular interest are redox flow batteries, which are rechargeable electrochemical energy storage devices that utilize the oxidation and reduction of two soluble electroactive species for charging (absorbing energy) and discharging (delivering energy).

Unlike conventional secondary batteries, the energy-bearing species are not stored within an electrode structure but in separate liquid reservoirs and pumped to and from the power converting device when energy is being transferred. Because of this key difference, flow battery systems can be more durable than conventional battery systems as electrode reactions are not accompanied by morphological changes due to the insertion or removal of the active species and can be more scalable than conventional battery systems as the energy capacity may be easily and inexpensively modulated by varying the reservoir volume or the species concentration, without sacrificing power density. Thus, while flow batteries may not compete with compact lithium (Li)-ion batteries for portable applications (e.g., cell phones, laptops) due to lower overall energy densities, they are well-suited for large-scale stationary applications.

Redox flow batteries (RFBs), which were developed in 1960s and 1970s, are among the leaders of large-scale energy storage technologies in performance. In RFBs, charge-storing materials dissolved in electrolyte solutions are stored in reservoirs and the electrochemical reactions occur in the reactor that is connected to the reservoirs through pipelines. Thus, RFBs have the potential for facile scale-up of energy capacity by increasing the volume of the reservoirs.

Since their inception in the 1960s, a large number of aqueous redox flow batteries have been developed including iron-chromium, bromine-polysulfide, vanadium-bromine, and all-vanadium systems. Several aqueous hybrid systems also have been developed, where one or both electrode reactions are a deposition/dissolution process, such as zinc-bromine and soluble lead-acid systems. Though several of these aqueous technologies have been successfully demonstrated at the megawatt-scale, none have experienced widespread commercialization due to low energy densities, low round-trip energy efficiencies, and high costs. Non-aqueous redox flow electrolytes also have been examined, which can offer a wider window of electrochemical stability, and in turn, can enable some flow batteries to operate at higher cell potentials (e.g., >2 V).

Despite the potential advantages of RFBs, it has been difficult to identify energy-dense charge-storing materials that can mitigate the engineering challenges and economic burden of grid-scale RFBs. From the perspective of materials development, liquid charge-storing materials could be a feasible solution to energy-dense RFBs by improving the solubility or enabling a solvent-lean RFB.

A pioneer of liquid charge-storing material was 1,4-di-tert-butyl-2-methoxy-5-(2-rnethoxyethoxy)benzene (DBM-MEB), which was developed Argonne National laboratory. This molecule demonstrates high stability in all charge states and excellent cyclability in RFBs. Despite its excellent performance, the solubility of bulky DBMMEB in a carbonate-based electrolyte is only 0.6 M, and the high viscosity of DBMMEB at room temperature restricts its applicability to solvent-lean systems.

Current flow battery designs have functional or cost-performance limitations that hamper large scale adoption of this technology. Thus, there is an ongoing need for new redox molecules for flow batteries. The redox materials and batteries described herein address this need.

SUMMARY OF THE INVENTION

Organic redox molecules that are poly(alkylene glycol) derivatives of 2,2,6,6-tetramethylpiperidine-1-oxyl (TEMPO) are described herein. The TEMPO derivatives can be utilized in a redox flow battery systems, e.g., as the redox reactant of a catholyte. In some embodiments the TEMPO derivatives are compounds of Formula (I):

(I)

wherein x is an integer from 1 to 8 (e.g., 1, 2, 3, or 4); R' is alkyl (e.g., $C_1$ to $C_4$ alkyl) or substituted-alkyl; each R" independently is selected from the group consisting of H, alkyl (e.g., $C_1$ to $C_4$ alkyl), substituted-alkyl, and halogen (e.g., F, Cl, Br); and each substituted-alkyl independently is alkyl (e.g., $C_1$ to $C_4$ alkyl) in which one or more hydrogen thereof is substituted by one or more moiety selected from the group consisting of —F, —Cl, —Br, —CN, —CF$_3$, alkenyl (e.g., $C_2$ to $C_5$ alkenyl such as —CH=CH$_2$, —CH=C(CH$_3$)$_2$, —CH=CHCH$_3$, and the like), alkynyl (e.g., $C_2$ to $C_5$ alkynyl such as —C≡CH, —C≡CCH$_3$, —C≡CH$_2$CH$_3$, and the like), —C(=O)OH, —C(=O)H, —C(=O)R''', —OR''', —SH, —SR''', —NH$_2$, —NHR''', —NR'''$_2$, —SiR'''$_3$, —OSiR'''$_3$, —S(O)OH, and —P(O)(OH)$_2$; and wherein R''' is alkyl or aryl (e.g., phenyl).

In some embodiments, each R" is H. In other embodiments, R' is $C_1$ to $C_4$ alkyl (e.g., methyl (Me), ethyl (Et), propyl (Pr), isopropyl (iPr), butyl (Bu), tert-butyl (tBu), and the like). In some other preferred embodiments, each R" is H, and R' is $C_1$ to $C_4$ alkyl (e.g., methyl or ethyl).

In some preferred embodiments, the redox compounds are represented by Formula (II):

(II)

wherein y is 1, 2, or 3; and R* is $C_1$ to $C_4$ alkyl, which is equivalent to Formula (I) in which R" is H, and R' is $C_1$ to $C_4$ alkyl, preferably methyl or ethyl.

The compounds of Formula (I) are soluble or miscible in polar organic and aqueous solvents and have redox properties substantially similar to TEMPO. Surprisingly, the compounds of Formula (II) also are liquids at room temperature and are miscible with polar solvents such as acetonitrile and water.

In another aspect, a flow battery comprises a cathode (also referred to as a "positive electrode") immersed in a liquid catholyte (also referred to as a "positive electrolyte") including a first redox reactant, an anode (also referred to as "negative electrode") immersed in an liquid anolyte (also referred to as a "negative electrolyte") comprising a second redox reactant (also referred to as a "negative redox reactant"). A cation-permeable separator (e.g., a membrane or other cation-permeable material) between the anolyte chamber and the catholyte chamber partitions the cathode and catholyte from the anode and anolyte. The anolyte and catholyte collectively can be referred to as "electrolytes" for convenience.

During charging and discharging, the electrolytes are circulated over their respective electrodes, while cations shuttle across the membrane between the two electrolytes to balance the charges that develop due to oxidation and reduction of components in the electrolytes. The anode and cathode act as current collectors for the electrons involved in the redox reactions. The cation-permeable separator membrane is adapted to allow cations (supplied, e.g., a salt or salts in one or more of the electrolytes) to cross the membrane and balance out charges in the anolyte and catholyte that develop during the charging and discharging of the battery. The redox reactant of catholyte comprises a compounds of Formula (I) as described herein, such as a compound of Formula (II).

In some embodiments, the catholyte comprises the compound of Formula (I) dissolved in an aqueous solvent (e.g., water or a mixture of water with a water-miscible organic solvent). In other embodiments the catholyte comprises the compound of Formula (I) dissolved in an organic solvent. In other embodiments, the catholyte comprises the compound of Formula (I) without any additional solvent.

The following non-limiting embodiments are provided to illustrate various aspects and features of the redox flow batteries described herein.

Embodiment 1 is a compound of Formula (I):

(I)

wherein x is an integer from 1 to 8; R' is alkyl or substituted-alkyl; each R" independently is selected from the group consisting of H, alkyl, substituted-alkyl, and halogen; and each substituted-alkyl independently is an alkyl in which one or more hydrogen thereof is substituted by one or more moiety selected from the group consisting of —F, —Cl, —Br, —CN, —$CF_3$, alkenyl, alkynyl, —C(=O)OH, —C(=O)H, —C(=O)R''', —OR''', —SH, —SR''', —$NH_2$, —NHR''', —NR'''$_2$, —SiR'''$_3$, —OSiR'''$_3$, —S(O)OH, and —P(O)(OH)$_2$; and R''' is alkyl or aryl.

Embodiment 2 is the compound of Embodiment 1, wherein x is 1, 2, or 3.

Embodiment 3 is the compound of Embodiment 1 or 2, wherein R' is $C_1$ to $C_4$ alkyl, and each R" independently is H or $C_1$ to $C_4$ alkyl.

Embodiment 4 is the compound of any one of Embodiments 1 to 3, wherein each R" is H.

Embodiment 5 is the compound of any one of Embodiments 1 to 4, wherein R' is methyl or ethyl.

Embodiment 6 is the compound of any one of Embodiments 1 to 5, wherein at least one of R" is a halogen.

Embodiment 7 is the compound of any one of Embodiments 1 to 6, wherein at least one of R" is F.

Embodiment 8 is the compound of any one of Embodiments 1 to 7, wherein each R" is F.

Embodiment 9 is the compound of Embodiment 1, wherein x is 1, 2, or 3, R' is methyl, and each R" is H.

Embodiment 10 is a redox flow battery comprising:

(a) a cathode within a catholyte chamber;

(b) a catholyte reservoir in fluid-flow connection with the catholyte chamber;

(c) an anode within an anolyte chamber;

(d) an anolyte reservoir in fluid-flow connection with the anolyte chamber;

(e) a catholyte comprising a first redox reactant within the catholyte reservoir and the catholyte chamber;

(f) an anolyte comprising a second redox reactant within the anolyte reservoir and the anolyte chamber; and (g) an ion-permeable separator membrane forming at least a portion of a common wall between the anolyte chamber and the catholyte chamber;

wherein:

the catholyte within the catholyte chamber contacts the cathode and the separator membrane;

the anolyte within the anolyte chamber contacts the anode and the separator membrane;

the first redox reactant has a higher redox potential than the redox potential of the second redox reactant;

and the first redox reactant comprises a compound of Formula (I):

wherein x is an integer from 1 to 8; R' is alkyl or substituted-alkyl; each R" independently is selected from the group consisting of H, alkyl, substituted-alkyl, and halogen; and each substituted-alkyl independently is alkyl in which at least one hydrogen thereof is substituted by one or more moiety selected from the group consisting of —F, —Cl, —Br, —CN, —$CF_3$, alkenyl, alkynyl, —C(=O)OH, —C=OH, —C(=O)R''', —OR''', —SH, —SR''', —$NH_2$, —NHR''', —$NR'''_2$, —$SiR'''_3$, —$OSiR'''_3$, —S(O)OH, and —P(O)$(OH)_2$; and wherein R''' is alkyl or aryl;

and wherein, during charging and discharging of the redox flow battery, the anolyte and the catholyte are circulated through the anolyte chamber and the catholyte chamber, respectively, while cations from the anolyte and catholyte shuttle through the separator membrane to balance the charges that develop within the anolyte and catholyte due to oxidation and reduction of the first and second redox reactants.

Embodiment 11 is the redox flow battery of Embodiment 10, wherein x is 1, 2, or 3.

Embodiment 12 is the redox flow battery of Embodiment 10 or 11, wherein R' is $C_1$ to $C_4$ alkyl, and each R" independently is H or $C_1$ to $C_4$ alkyl.

Embodiment 13 is the redox flow battery of any one of Embodiments 10 to 12, wherein each R" is H.

Embodiment 14 is the redox flow battery of any one of Embodiments 10 to 13, wherein R' is methyl or ethyl.

Embodiment 15 is the redox flow battery of any one of Embodiments 10 to 14, wherein at least one of R" is a halogen.

Embodiment 16 is the redox flow battery of any one of Embodiments 10 to 15, wherein at least one of R" is F.

Embodiment 17 is the redox flow battery of any one of Embodiments 10 to 16, wherein each R" is F.

Embodiment 18 is the redox flow battery of any one of Embodiments 10 to 17, wherein the compound of Formula (I) is dissolved in a non-aqueous polar organic solvent or an aqueous solvent.

Embodiment 19 is the redox flow battery of any one of Embodiments 10 to 18, wherein the second redox reactant comprises at least one material selected from the group consisting of a quinoxaline compound, a dipyridyl ketone compound, a viologen compound, a benzophenone compound, an anthraquinone compound, and a redox active metal ion.

Embodiment 20 is the redox flow battery of any one of Embodiments 10 to 19, wherein the cations comprise one or more cations selected from the group consisting of a hydrogen cation, ammonium cation, an alkali metal ion, an alkaline earth metal ion, a transition metal cation, and an organic cation.

Embodiment 21 is the redox flow battery of Embodiment 10, wherein x is 1, 2, or 3, R' is methyl, and each R" is H.

The compounds of Formula (I) can be used as a redox reactant in the catholyte of a redox flow battery at low solvent loading or even in the absence of a solvents, thereby providing significantly higher energy storage densities compared to conventional redox flow batteries. This is possible due to the high redox reactant concentrations that are obtainable with the compounds of Formula (I), as well as their excellent cycling stability.

BRIEF DESCRIPTION OF THE DRAWINGS

The following non-limiting drawing figures are provided to illustrate certain aspects and features of the compositions and batteries described herein.

DETAILED DESCRIPTION OF THE PREFERRED EMBODIMENTS

The present invention relates to TEMPO derivatives that are useful as redox reactants in redox flow batteries. The present invention also relates to redox flow batteries comprising the TEMPO derivatives.

The TEMPO derivatives described herein are 4-poly (alkylene glycol)-TEMPO derivatives of Formula (I):

wherein x is an integer from 1 to 8; R' is alkyl or substituted-alkyl; each R" independently is selected from the group consisting of H, alkyl, substituted-alkyl, and halogen; and each substituted-alkyl independently is an alkyl in which one or more hydrogen thereof is substituted by one or more moiety selected from the group consisting of —F, —Cl, —Br, —CN, —CF$_3$, alkenyl, alkynyl, —C(=O)OH, —C(=O)H, —C(=O)R''', —OR''', —SH, —SR''', —NH$_2$, —NHR''', —NR'''$_2$, —SiR'''$_3$, —OSiR'''$_3$, —S(O)OH, and —P(O)(OH)$_2$; and R''' is alkyl or aryl.

In some preferred embodiments, a flow battery comprises, consists essentially of, or consists of a negative electrode immersed in a flowing liquid anolyte, a positive electrode immersed in a flowing liquid catholyte, and a cation-permeable separator to allow cations to shuttle between the anolyte and the catholyte during charging and discharging of the battery. The negative electrode and positive electrode each act as current collectors. The catholyte includes a first redox reactant which comprises a compound of Formula (I), and the anolyte comprises a second redox reactant. Each electrolyte comprises a cation that can migrate through the cation-permeable membrane. In some embodiments, the redox reactant of the anolyte is dissolved in a solvent (e.g., a aqueous or non-aqueous solvent), while the compound of Formula (I) in the catholyte can be present neat, or dissolved in a solvent. The redox reactant of the anolyte is selected to have a lower redox potential than the redox potential of the compound of Formula (I) in the catholyte. The cation components of the electrolytes shuttle between the anolyte and the catholyte through the cation-permeable separator to balance charges that develop during the oxidation and reduction of the redox reactants. The flow battery is operated by pumping the anolyte and catholyte across their respective electrodes.

The redox reactant of the anolyte can be present at a concentration in the range of about 0.01 to about 5 M. In some embodiments, the redox reactant is present in the anolyte at a concentration in the range of about 0.1 M to about 2 M The compound of Formula (I) can be present in the catholyte either neat, or dissolved in a solvent at a concentration in the range of about 0.01 M to about 5 M. In some embodiments, the compound of Formula (I) is present in the catholyte at a concentration in the range of about 0.1 M to about 2 M.

Organic solvents that can be used in the anolytes and catholytes described herein can be composed of a single solvent or a combination of two or more solvents. The solvent or solvents of the anolyte can be the same as the solvent or solvents of the catholyte, or the anolyte and catholyte can comprise different solvents. Any electrochemically stable polar organic solvents that are suitable for use in battery electrolytes, for example, can be utilized. Such solvents are well known in the battery art, and include, for example, organic carbonates (e.g., ethylene carbonate, propylene carbonate, ethyl methyl carbonate, and the like), ethers (e.g., diethyl ether, tetrahydrofuran, 2-methyl tetrahydrofuran, dimethoxyethane, and 1,3 dioxolane), esters (e.g., methyl formate, gamma-butyrolactone, and methyl acetate), sulfones (e.g., ethyl methyl sulfone or sulfolane), sulfoxides (e.g., dimethyl sulfoxide or diethyl sulfoxide), and nitriles (e.g., acetonitrile). In some embodiments, the solvents comprise, consist essentially of, or consist of one or more organic carbonates such as ethylene carbonate (EC), propylene carbonate (PC), dimethyl carbonate (DMC), diethyl carbonate (DEC), ethyl methyl carbonate (EMC), or a combination of two or more of the foregoing carbonates.

Examples of some suitable carbonate solvents include propylene carbonate, and mixtures of ethylene carbonate and ethyl methyl carbonate in an EC/EMC in a volume or weight ratio of about 3/7.

The cations of the electrolytes can be any monovalent (e.g., Li$^+$, Na$^+$, Ag$^+$, Cu$^+$, NH$_4^+$, H$^+$ (e.g., hydronium ion), and the like) or multivalent cation (e.g., Mg$^{2+}$, Ca$^{2+}$, Cu$^{2+}$, Zn$^{2+}$, and the like). In some preferred embodiments, the cation comprises a hydrogen cation (e.g., a proton or hydronium ion), ammonium cation, an alkali metal ion, an alkaline earth metal ion, a transition metal cation, and/or an organic cation. Non-limiting examples of alkali metal cations include lithium and sodium. Non-limiting examples of alkaline earth metal ions include magnesium and calcium. Non-limiting examples of organic cations include tetraalkyl ammonium ions and pyridinium ions. Anions present in the electrolytes, e.g., as counter ions to the cations, can be any electrochemically stable anion suitable for use in battery electrolytes. Some non-limiting examples of suitable anions include tetrafluoroborate ion (BF$_4^-$), hexafluorophosphate ion (PF$_6^-$), perchlorate ion (ClO$_4^-$), hexafluoroarsenate ion (AsF$_6^-$), trifluoromethanesulfonate ("triflate" or CF$_3$SO$_3^-$) ion, bis(perfluoroethanesulfonyl) imide (BETI) ion (N(SO$_2$CF$_2$CF$_3$)$^{2-}$), bis(oxalato)borate (BOB) ion (B(C$_2$O$_4$)$^{2-}$), a halogen-substituted borane (B$_{12}$X$_n$H$_{(12-n)}^{2-}$; X=halogen) ion, and bis(trifluoromethanesulfonyl)imide (TFSI) ion (i.e., N(SO$_2$CF$_3$)$_2^-$). In some embodiments, the cation is a proton or hydronium ion supplied by an aqueous acid (e.g., sulfuric acid, phosphoric acid, and the like). In some embodiments, the cation is a an alkaline earth cation from an alkali metal halide (e.g., sodium chloride, and the like).

In some embodiments, the redox reactant of the anolyte can be, e.g., a quinoxaline compound (e.g., a quinoxaline compound bearing at least one electron-donating substituent), a dipyridyl ketone compound, a viologen compound (e.g., a bis-benzyl viologen salt, a bis-ethyl viologen salt, a bis-methyl viologen salt, and the like), a benzophenone compound, an anthraquinone compound (e.g., anthraquinone-2,7-disulfonic acid salts (AQDS), 9,10-anthraquinone-2,6-disulfonic acid, anthraquinone-2-sulfonic acid salts (AQS), anthraflavic acid (2,6-dihydroxyanthraquinone)), a redox active metal ion (e.g., a vanadium ion), and/or other such materials, such as, e.g., materials disclosed by Winsberg et al., *Angewandte Chemie Int. Ed.;* 2017, 56:686-711, which is incorporated herein by reference in its entirety. As used herein, the term "viologen compound" refers to N-alkylated 4,4'-bipyridyl salts comprising cations with the formula (C$_5$H$_4$NR)$_2^{2+}$ where R is, e.g., alkyl, benzyl, and the like. In some viologens, the pyridyl groups are further modified.

Optionally, the redox reactant of the catholyte in some embodiments also can include another redox reactant in addition to the compound of Formulas (I), such as, e.g., a 1,4-dialkoxybenzene compound (e.g., a 2,5-di-tert-butyl-1, 4-dialkoxybenzene compound), a phenothiazine compound, a catechol ether compound, a catecholborane compound (e.g., a halogenated 5-phenyl-1,3,2-benzodioxaborole compound), a borane cluster compound (e.g., a halogen-substituted B$_{12}$ borane compound), a 1,3 benzodioxole compound (e.g., a 4,6-di-tert-butyl-1,3-benzodioxole), a benzodioxin compound (e.g., a 5,7-di-tert-butyl-benzodioxin, a 1,4-dialkoxy-2,5 bisphosphinyl benzene compound, a 1,4-phenylene diphosphate ester compound (e.g., a 2,5-di-tert-butyl-1,4-phenylene diphosphate ester), and/or a phenazine compound.

Figure 1:
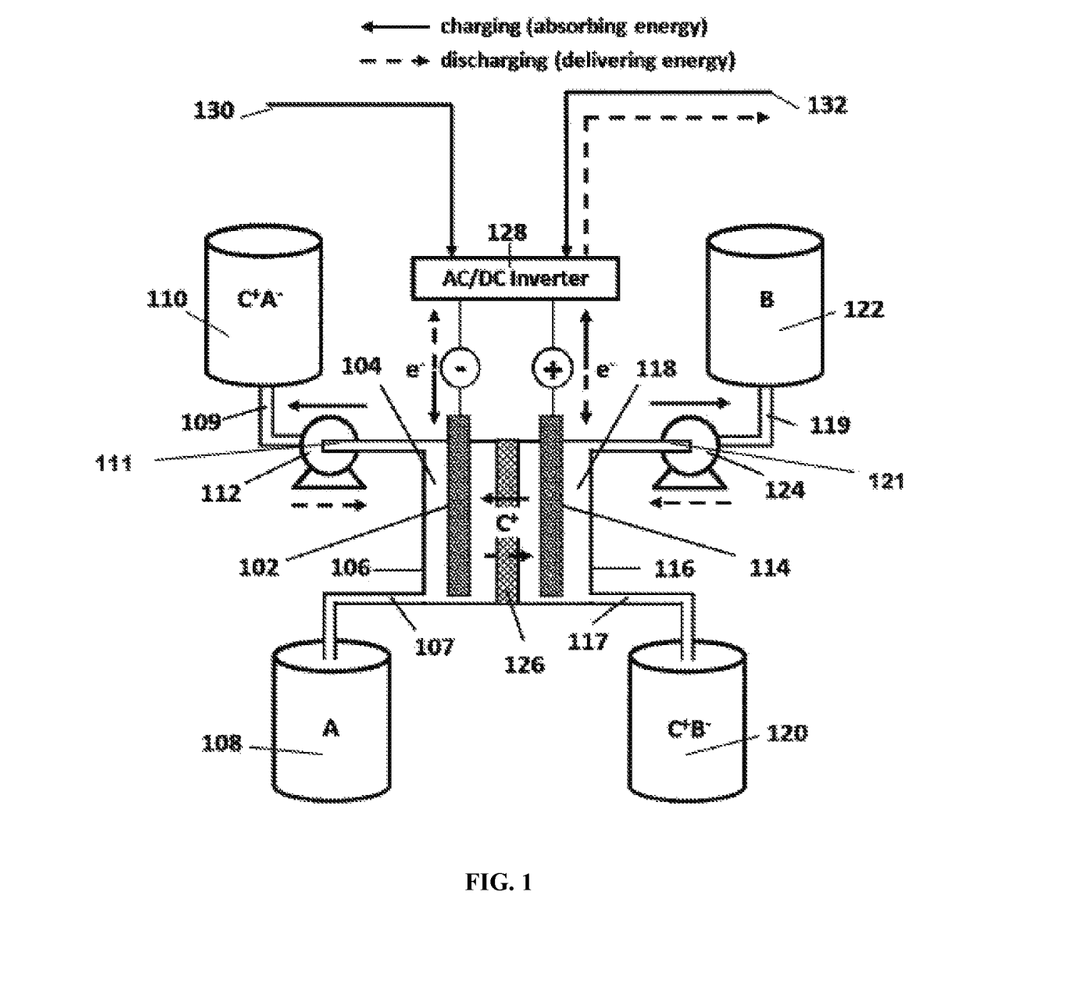
FIG. 1 provides a schematic illustration of an exemplary redox flow battery suitable for large-scale electrochemical energy storage. Species A and B represent generic negative and positive redox reactant electrode materials, respectively. Species $C^+$ represents a cation, which shuttles across a separator to maintain electroneutrality.

FIG. 1 schematically illustrates a redox flow battery design. The redox flow battery comprises negative electrode 102 within negative electrolyte chamber (anolyte chamber) 104, defined by housing 106. First negative electrolyte reservoir (anolyte reservoir) 108 is in fluid-flow communication with anolyte chamber 104 via pipe 107. Second anolyte reservoir 110 is operably connected to pump 112 via pipe 109, while pump 112 also is operably connected to anolyte chamber 104 via pipe 111. Pump 112 is adapted to facilitate transfer of negative electrolyte (anolyte) back and forth between first anolyte reservoir 108 to second anolyte reservoir 110 through anolyte chamber 104, such that the flowing electrolyte contacts negative electrode 102. The battery also includes a positive electrode 114 within positive electrolyte chamber (catholyte chamber) 118, defined by housing 116. First positive electrolyte reservoir (catholyte reservoir) 120 is in fluid-flow communication with catholyte chamber 118 via pipe 117. Second catholyte reservoir 122 is operably connected to pump 124 via pipe 119, while pump 124 also is operably connected to catholyte chamber 118 via pipe 121. Pump 124 is adapted to facilitate transfer of positive electrolyte (catholyte) back and forth between first catholyte reservoir 120 to second catholyte reservoir 122 through catholyte chamber 118, such that the flowing electrolyte contacts positive electrode 114. Cation-permeable separator 126 separates anolyte chamber 104 from catholyte chamber 118, and allows passage of cations ($C^+$) back and forth between the positive and negative electrolytes to balance out charges that form during oxidation and reduction of materials within the electrolytes.

During charging of the redox flow battery, an electric potential is applied to the negative electrode 102 and positive electrode 114, e.g., from an energy source 130 via AC/DC inverter 128, while simultaneously pumping the negative electrolyte over negative electrode 102 from first NE reservoir 108 to second NE reservoir 110, and simultaneously pumping the positive electrolyte over the positive electrode 114 from the first PE reservoir 120 to the second PE reservoir 122. Cations ($C^+$) pass through cation-permeable separator 126 to balance the charges. A negative redox reactant material (represented by $A/A^-C^+$) and a positive redox reactant material (represented by $B/B^-C^+$) in the electrolytes undergo redox reactions upon contact with the electrodes such that the reduced from of A is stored in second NE reservoir 110, while the oxidized form of B is stored in the second PE reservoir 122. In this way, energy can be stored by charging the battery from energy source 130 during off-peak usage periods.

During discharge, the electrodes are placed in a circuit (e.g., a power grid 132) and the direction of electrolyte flow is reversed, with the stored reduced negative electrolyte being pumped over negative electrode 102 back into first anolyte reservoir 108, and the stored oxidized positive electrolyte being pumped over positive electrode 114 back into first catholyte reservoir 120. Cations again transfer through cation-permeable separator 126 (in the opposite direction) to balance the charges resulting from redox reactions at the electrodes. The energy stored in the system during charging can thus be directly used to perform work or can be transferred into power grid 132 during peak usage periods to supplement the power supply. AC/DC inverter 128 again can be used to facilitate transfer of energy to an AC power grid.

Figure 2:
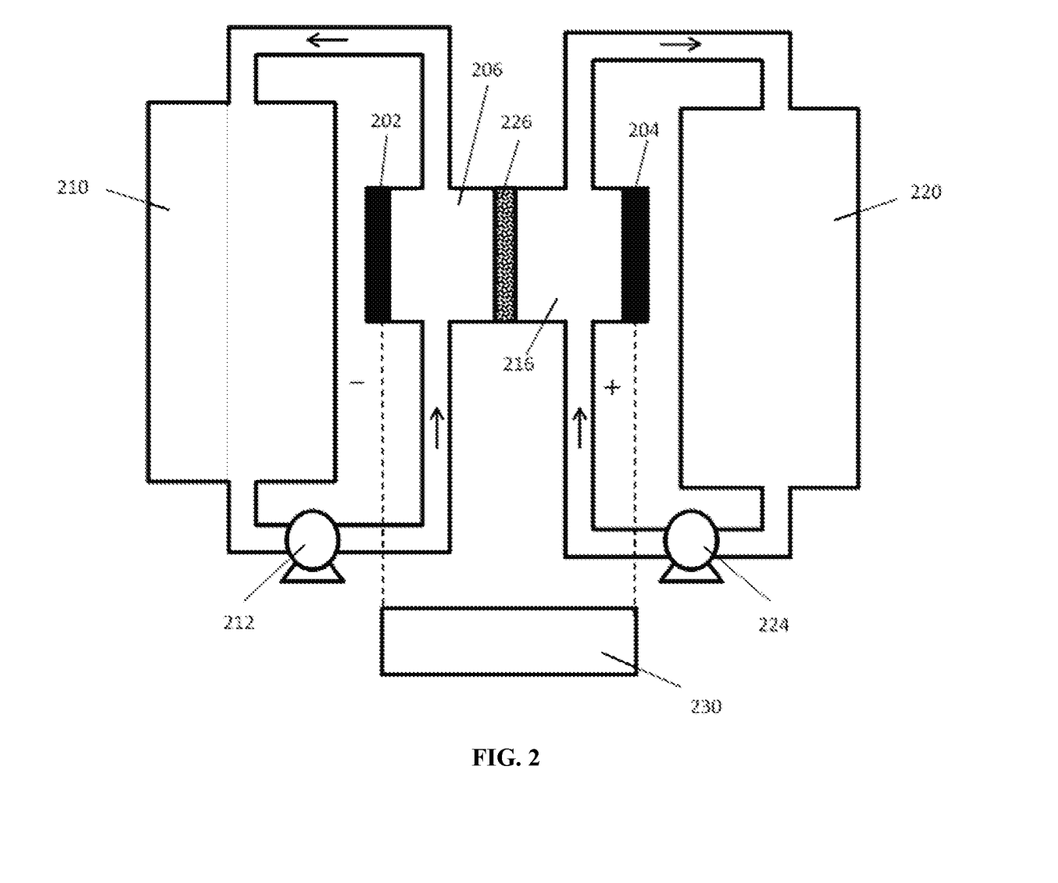
FIG. 2 provides a schematic illustration of an alternative exemplary redox flow battery suitable for large-scale electrochemical energy storage.

FIG. 2 schematically illustrates another redox flow battery design. The redox flow battery comprises anode 202 within anolyte chamber 206. Anolyte storage tank or reservoir 210 is in fluid-flow communication with anolyte chamber 206, and pump 212 is adapted to circulate anolyte through anolyte chamber 206, such that the flowing anolyte contacts anode 202. The battery also includes a cathode 204 within catholyte chamber 216. Catholyte storage tank or reservoir 220 is in fluid-flow communication with catholyte chamber 216, and pump 224 is adapted to circulate catholyte through catholyte chamber 216, such that the flowing catholyte contacts cathode 204. Cation-permeable separator membrane 226 separates anolyte chamber 206 from catholyte chamber 216, and allows passage of cations (e.g., $H+$, $Li+$, $Na+$, and the like) back and forth between the anolyte and catholyte to balance out charges that form during oxidation and reduction of the redox materials within the anolyte and catholyte.

During charging of this redox flow battery design, an electric potential is applied to the anode 202 and cathode 204, e.g., from an energy source 230, e.g., via an AC/DC inverter, while simultaneously pumping the anolyte through anolyte chamber 206 from anolyte reservoir 210, and simultaneously pumping the catholyte through catholyte chamber 216 from catholyte reservoir 220. The electrical potential across the anode and cathode causes redox reactions of the redox reactants in the anolyte (reduction) and catholyte (oxidation), while cations pass through cation-permeable separator 226 to balance the charges that develop due to the redox reactions. The anolytes and catholytes are circulated back into their respected reservoirs (210 and 220) so that the concentration of the reduced anolyte builds up in the circulating anolyte solution and the concentration of oxidized catholyte builds up in the circulating catholyte solution. In this way, energy can be stored by charging the battery from energy source 230 during off-peak usage periods.

During discharge, the electrodes 202 and 204 are placed in a circuit (e.g., with a power grid) and the reduced anolyte is pumped through the anolyte chamber 206, while the oxidized catholyte is pumped through the catholyte chamber 216. Cations again transfer through cation-permeable separator 226 (in the opposite direction) to balance the charges resulting from redox reactions at the electrodes induced by the load from the circuit. As the battery discharges, the reduced anolyte is oxidized back to its original form and the oxidized catholyte is reduced back to its original form. The energy stored in the system during charging can thus be directly used to perform work or can be transferred into the circuit (e.g., the power grid). An AC/DC inverter again can be used to facilitate transfer of energy to an AC power grid. Once fully or partially discharged, the charging and discharging cycles can be repeated.

The negative and positive electrodes (anode and cathode, respectively) each can comprise, consist essentially of, or consist of a metal (e.g., platinum, copper, aluminum, nickel or stainless steel), a carbon material (e.g., carbon black, activated carbon, amorphous carbon, graphite, graphene, or a nanostructured carbon material), or a combination thereof. The electrodes can be porous, fluted, or smooth.

Pumps suitable for use in the flow batteries described herein include internal gear pumps, screw pumps, shuttle block pumps, flexible vane pumps, sliding vane pumps, circumferential piston pumps, helical twisted root pumps, piston pumps, diaphragm pumps, peristaltic pumps, centrifugal pumps, and the like, which are well known in the liquid pumping art. The utility of a given pump will be dependent on the chemical resistance of the pump to the electrolyte components in contact therewith (i.e., materials compatibility).

A cation-permeable separator membrane is situated between the anolyte chamber and the catholyte chamber and forms a common wall (or at least part of a common wall) between the two chambers. The separator is adapted to allow cations to flow back and forth between the negative and positive electrolytes upon charging and discharging of the battery. The separator can be, for example, a cation-permeable membrane, sheet, panel, or film that is permeable to the cations of the electrolytes. In some embodiments, the separator is at least partially impermeable to the redox components of the electrolytes, although this is not an absolute requirement for the batteries of the present invention.

Non-limiting examples of suitable separator materials include, NAFION® type ion exchange membranes (sulfonated tetrafluoroethylene-based fluoropolymer-copolymers), other porous polymeric materials such as, for example, sulfonated poly(ether ketones), polysulfones, polyethylene, polypropylene, ethylene-propylene copolymers, polyimides, polyvinyldifluorides, and the like, which can be in the form of membranes, matrix-supported gels, sheets, films, or panels. Other suitable materials include porous ceramics, porous insulated metals, cation-conducting glasses, and zeolites. Alternatively, the separator can be an interface between immiscible liquids. In such case, a porous film, panel, or mesh might be included to aid in maintaining separation between the liquids (e.g., as a physical support or guide to aid in maintaining laminar flow at the interface).

The compounds of Formula (I) described herein can be readily synthesized by alkylation of the hydroxyl group of 4-hydroxy-TEMPO with a suitable poly(alkylene glycol) alkylating agent. Three examples of the compounds of Formula (I) are illustrated below in Scheme 1.

Scheme 1.

TEMPO-EG1    TEMPO-EG2    TEMPO-EG3

In Scheme 1, TEMPO-EG1 includes a methoxyethoxy group at position 4 of the TEMPO ring, (i.e., 4-(2-methoxyethoxy)-2,2,6,6-tetramethylpiperidine-1-oxyl, also known as 4-(3-oxabutyloxy)-2,2,6,6-tetramethylpiperidine-1-oxyl), which is a compound of Formula (I) where R" is H, R' is methyl, and x is 1. TEMPO-EG2 is 4-(3,6-dioxaheptyloxy)-2,2,6,6-tetramethylpiperidine-1-oxyl, which is a compound of Formula (I) where R" is H, R' is methyl, and x is 2. TEMPO-EG3 is 4-(3,6,9-trioxadecyloxy)-2,2,6,6-tetramethylpiperidine-1-oxyl, which is a compound of Formula (I) where R" is H, R' is methyl, and x is 3.

TEMPO-EG1 can be synthesized by alkylation of 4-hydroxy-TEMPO with 1-bromo-2-methoxyethane, which involves deprotonation of 4-hydroxy-TEMPO with a strong base (e.g., NaH) in a polar aprotic solvent (e.g., dimethylformamide (DMF)), followed by addition of 1-bromo-2-methoxyethane. These same conditions were not useful for the synthesis of TEMPO-EG2 and TEMPO-EG3 from the corresponding bromo compounds (i.e., 1-bromo-3,6-dioxaheptane and 1-bromo-3,6,9-trioxadecane, respectively), because the elimination of HBr predominated over alkylation for those materials. Use of the corresponding 1-tosyl poly(alkylene glycol) compounds (i.e., TsO—(CR"$_2$CR"$_2$O)$_x$R') in place of the bromo compounds eliminated this problem.

The following non-limiting examples are provided to illustrate certain features and aspects of the redox flow batteries described herein.

Example 1. Preparation of 4-(1,4-dioxabutyl)-2,2,6,6-tetramethylpiperidine-1-oxyl (TEMPO-EG1)

4-Hydroxy-2,2,6,6-tetramethylpiperidine 1-oxyl (4-Hydroxy TEMPO) (5 g, 29 mmol) was dissolved in 80 ml of dimethylformamide (DMF) and cooled to 0° C. Sodium hydride (1.16 g, 29 mmol, 60 wt % in mineral oil) was added to the reaction mixture slowly. Then, the reaction mixture was vigorously stirred at 0° C. until no bubbles were observed. The reaction mixture was warmed up to room temperature and 1-bromo-2-methoxyethane (8.06 g, 58 mmol) was added. The reaction progress was monitored by GC-MS. When the reaction was complete, the reaction mixture was quenched in ice water and exacted with dichloromethane. The organic phase was rinsed with saturated NaCl aqueous solution multiple times. The crude product was purified via silica flash chromatography using an eluent of ethyl acetate and hexanes (1:9, v/v). The pure product was a red liquid (76%, 5.1 g).

Example 2. Preparation of 4-(1,4,7-trioxaoctyl)-2,2,6,6-tetramethylpiperidine-1-oxyl (TEMPO-EG2)

4-Hydroxy TEMPO (5 g, 29 mmol) was dissolved in 80 ml of DMF and cooled to 0° C. Sodium hydride (1.16 g, 29 mmol, 60 wt % in mineral oil) was added to the reaction mixture slowly. Then, the reaction mixture was vigorously stirred at 0° C. until no bubbles were observed. The reaction mixture was warmed up to room temperature and 2-(2-methoxyethoxy)ethyl 4-methylbenzenesulfonate (7.13 g, 29 mmol) was added. The reaction progress was monitored by GC-MS. When the reaction was complete, the reaction mixture was quenched in ice water and exacted with dichloromethane. The organic phase was rinsed with saturated NaCl aqueous solution multiple times. The crude product was purified via silica flash chromatography using an eluent of ethyl acetate and hexanes (1:9, v/v). The pure product was a red liquid (86%, 6.1 g).

Example 3. Preparation of 4-(1,4,7,10-tetraxaundecyl)-2,2,6,6-tetramethylpiperidine-1-oxyl (TEMPO-EG3)

4-Hydroxy TEMPO (5 g, 29 mmol) was dissolved in 80 ml of DMF and cooled to 0° C. Sodium hydride (1.16 g, 29 mmol, 60 wt % in mineral oil) was added to the reaction mixture slowly. Then, the reaction mixture was vigorously stirred at 0° C. until no bubbles were observed. The reaction mixture was warmed up to room temperature and 2-(2-(2-methoxyethoxy)ethoxy)ethyl 4-methylbenzenesulfonate (8.27 g, 29 mmol) was added. The reaction progress was monitored by GC-MS. When the reaction was complete, the reaction mixture was quenched in ice water and exacted with dichloromethane. The organic phase was rinsed with saturated NaCl aqueous solution multiple times The crude product was purified via silica flash chromatography using an eluent of ethyl acetate and hexanes (1:9, v/v). The pure product was a red liquid (71%, 5.9 g).

Figure 3:
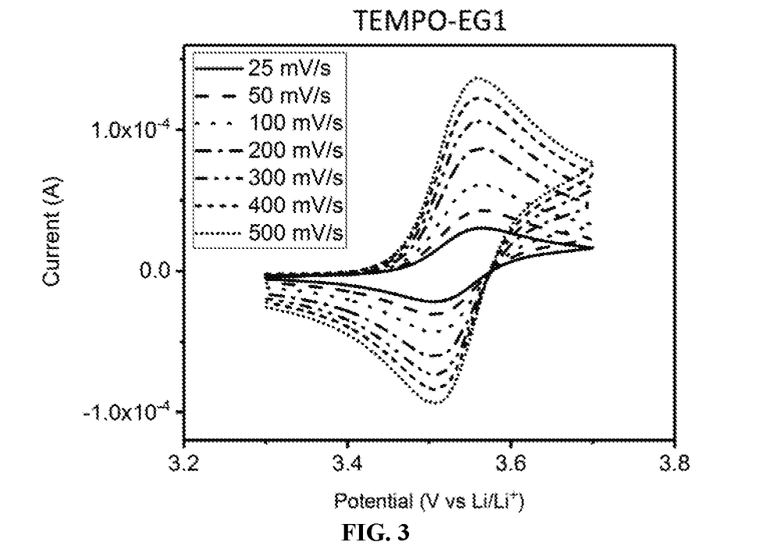
FIG. 3 shows cyclic voltammograms of 10 mM 4-(3-oxabutyloxy)-2,2,6,6-tetramethylpiperidine-1-oxyl (TEMPO-EG1) in a non-aqueous electrolyte (1.5 M $LiPF_6$ in a mixture of ethylene carbonate (EC) and ethyl methyl carbonate (EMC), 3:7 (v/v), respectively) at various scan rates given in mV/s.

Example 4. Electrochemical Evaluation of TEMPO-EG1, TEMPO-EG2 and TEMPO-EG3 in a Non-Aqueous Solvent FIG. 3 provides cyclic voltammograms of 10 mM 4-(1,4-dioxabutyl)-2,2,6,6-tetramethylpiperidine-1-oxyl (TEMPO-EG1) in a non-aqueous electrolyte (1.5 M LiPF$_6$ in a mixture of ethylene carbonate (EC) and ethyl methyl carbonate (EMC), 3:7 (v/v), respectively) at various scan rates given in mV/s. In FIG. 3, the cyclic voltammograms were measured at various rates with iR-correction applied. A glassy carbon electrode was used as the working electrode, while lithium metal strips were used as the counter and reference electrodes. TEMPO-EG1 exhibited a redox potential of 3.53 V vs. Li/Li$^+$.

Figure 4:
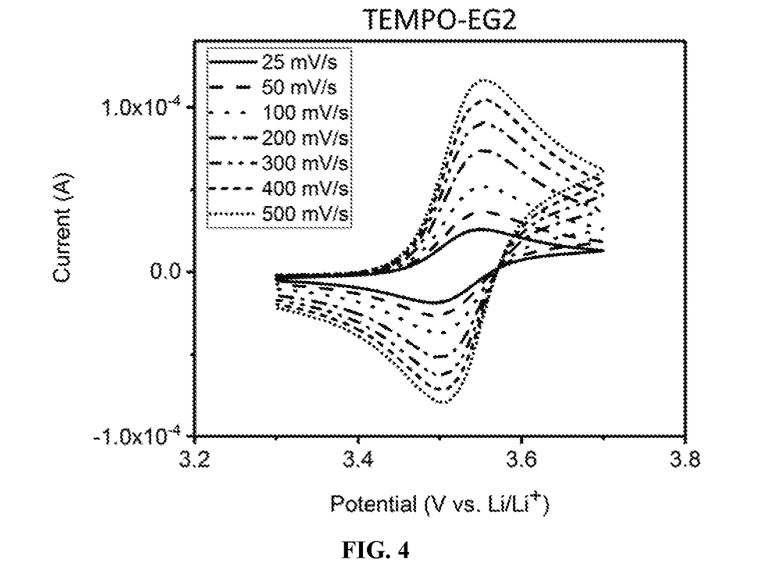
FIG. 4 shows cyclic voltammograms of 10 mM 4-(3,6-dioxaheptyloxy)-2,2,6,6-tetramethylpiperidine-1-oxyl (TEMPO-EG2) in a non-aqueous electrolyte (1.5 M $LiPF_6$ in a mixture of ethylene carbonate (EC) and ethyl methyl carbonate (EMC), 3:7 (v/v), respectively) at various scan rates given in mV/s.

FIG. 4 provides cyclic voltammograms of 10 mM 4-(1,4,7-trioxaoctyl)-2,2,6,6-tetramethylpiperidine-1-oxyl (TEMPO-EG2) in a non-aqueous electrolyte (1.5 M LiPF$_6$ in a mixture of ethylene carbonate (EC) and ethyl methyl carbonate (EMC), 3:7 (v/v), respectively) at various scan rates given in mV/s. In FIG. 4, the cyclic voltammograms were measured at various rates with iR-correction applied. A glassy carbon electrode was used as the working electrode, while lithium metal strips were used as the counter and reference electrodes. TEMPO-EG2 exhibited a redox potential of 3.53 V vs. Li/Li$^+$.

Figure 5:
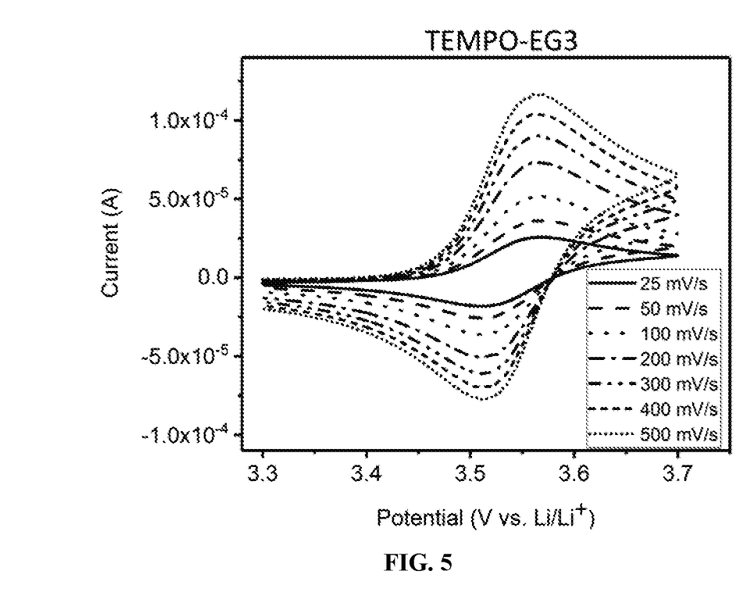
FIG. 5 provides cyclic voltammograms of 10 mM 4-(1,4,7,10-tetraoxaundecyl)-2,2,6,6-tetramethylpiperidine-1-oxyl (TEMPO-EG3) in a non-aqueous electrolyte (1.5 M $LiPF_6$ in a mixture of ethylene carbonate (EC) and ethyl methyl carbonate (EMC), 3:7 (v/v), respectively) at various scan rates given in mV/s.

FIG. 5 provides cyclic voltammograms of 10 mM 4-(1,4,7,10-tetraoxaundecyl)-2,2,6,6-tetramethylpiperidine-1-oxyl (TEMPO-EG3) in a non-aqueous electrolyte (1.5 M LiPF$_6$ in a mixture of ethylene carbonate (EC) and ethyl methyl carbonate (EMC), 3:7 (v/v), respectively) at various scan rates given in mV/s. In FIG. 5, the cyclic voltammograms were measured at various rates with iR-correction applied. A glassy carbon electrode was used as the working electrode, while lithium metal strips were used as the counter and reference electrodes. TEMPO-EG3 exhibited a redox potential of 3.53 V vs. Li/Li$^+$.

The results in FIGS. 3, 4, and 5 show nearly identical redox potentials of liquid TEMPO-EG1, TEMPO-EG2, and TEMPO-EG3 in the carbonate-based electrolytes. This observation demonstrates the minimal effects of the ether solubilizers on the electrochemical properties of the redox active core.

Example 5. Electrochemical Evaluation of TEMPO-EG3 in an Aqueous Solvents

Cyclic voltammograms of 10 mM TEMPO-EG3 in an aqueous electrolyte (1 M aqueous sulfuric acid) were measured at various scan rates given in mV/s. A Pt disk was used as the working electrode, while the counter electrode was a Pt coil and the reference electrode was Ag/AgCl. TEMPO-EG3 exhibited a redox potential of about 0.55 V vs. Ag/AgCl in the acidic electrolyte.

Cyclic voltammograms of 10 mM TEMPO-EG3 in an aqueous electrolyte (1M aqueous sodium chloride) were measured at various scan rates given in mV/s. A Pt disk was used as the working electrode, while the counter electrode was a Pt coil and the reference electrode was Ag/AgCl. TEMPO-EG3 exhibited a redox potential of about 0.59 V vs. Ag/AgCl in the neutral electrolyte.

The cyclic voltammetry results demonstrate excellent electrochemical reversibility of TEMPO-EG3 in common aqueous electrolytes. These observations demonstrate the applicability of using TEMPO-EG3 as the catholyte for the aqueous redox flow batteries.

Example 6. Viscosity Measurements of TEMPO-EG1, TEMPO-EG2 and TEMPO-EG3 in a Non-Aqueous Solvent The viscosities of liquid TEMPO derivatives were determined at 23.4° C. using a RHEOSENSE microfluidic and micro-electro-mechanical-systems (MEMS) viscometer. The RHEOSENSE viscometer is based on the viscometer-rheometer-on-a-chip (VROC) technology. For TEMPO-EG1 and EG2, shear rates were swept from 500 s$^{-1}$ to 5000 s$^{-1}$, while the viscosity of TEMPO-EG3 was measured from 100 s$^{-1}$ to 4000 s$^{-1}$. All liquid TEMPO derivatives displayed Newtonian behavior due to the independence of viscosities on shear rates. TEMPO-EG1 that has the shortest glycol ether chain shows the lowest viscosity. Longer glycol ether chains lead to increases in viscosity, but the impact differs drastically. The viscosity of TEMPO-EG2 (10.88 mPa·s) is almost the same as that of TEMPO-EG1 (10.23 mPa·s) while TEMPO-EG3 (21.30 mPa·s) shows a doubled value.

Example 7. Electrochemical Evaluation of TEMPO-EG1 in a Flow Cell

Figure 6:
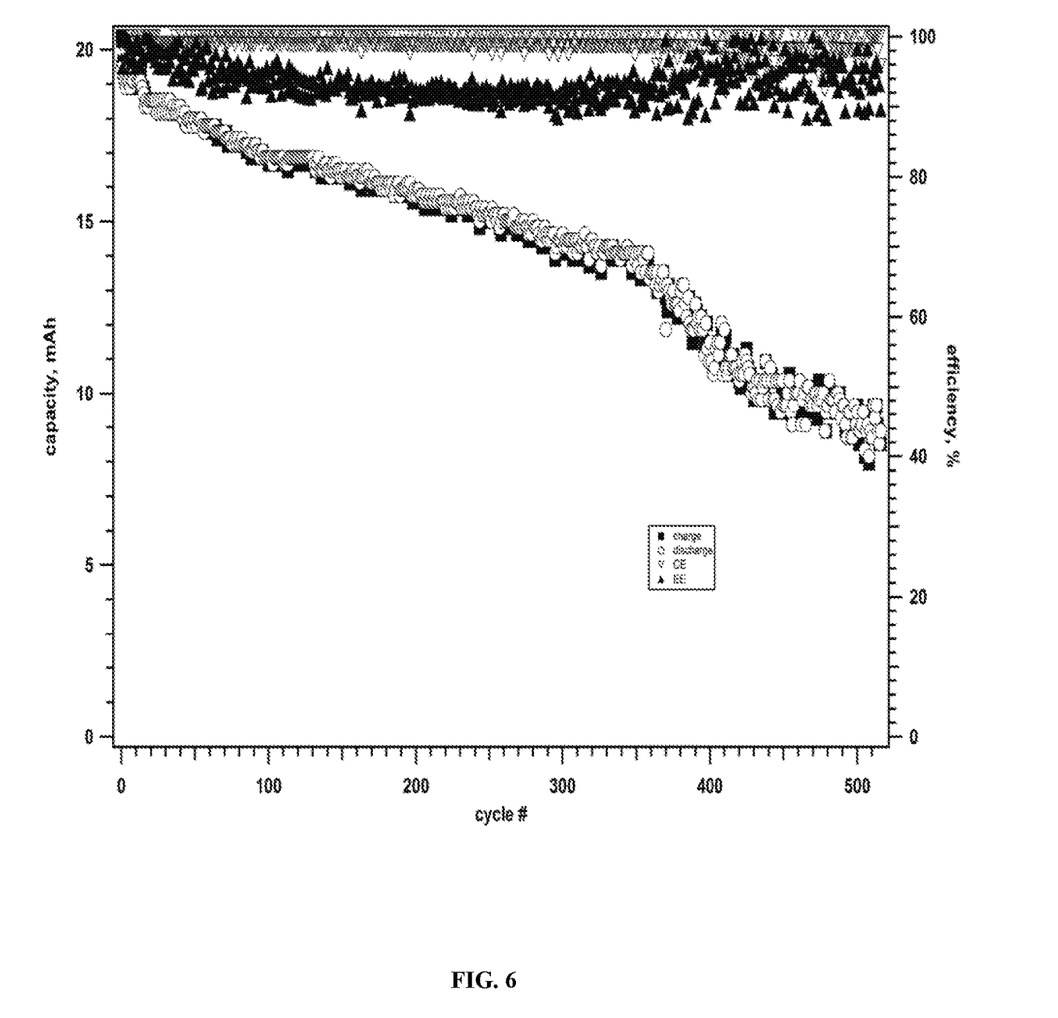
FIG. 6 provides plots of capacity (left vertical axis) and efficiency (right vertical axis) versus cycle number (horizontal axis) for 0.25 M TEMPO-EG1 in 0.5 M lithium bis(trifluoromethanesulfonyl)imide (TFSI) in acetonitrile at 5 C cycling rate.

FIG. 6 provides plots of capacity (left vertical axis) and efficiency (right vertical axis) versus cycle number (horizontal axis) for 0.25 M TEMPO-EG1 in 0.5 M lithium bis(trifluoromethanesulfonyl)imide (TFSI) in acetonitrile at a 5 C cycling rate. In FIG. 6, carbon papers were used the electrodes while the separator was a CELGARD 2325 membrane. The circulation rate of the electrolytes was 20 ml/min.

Figure 7:
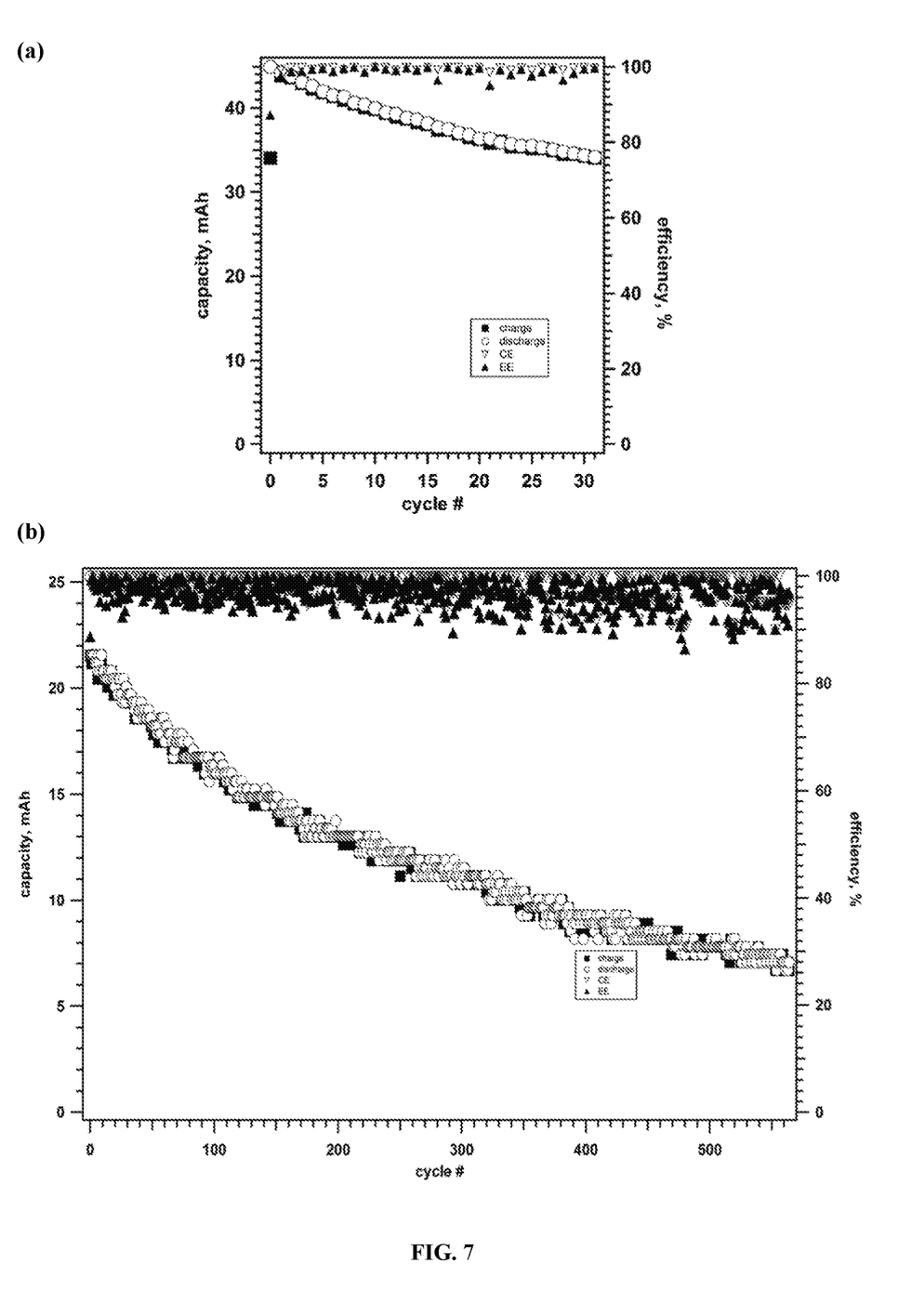
FIG. 7 provides plots of capacity (left vertical axis) and efficiency (right vertical axis) versus cycle number (horizontal axis) for 0.5 M TEMPO-EG1 in 1 M tetraethyl ammonium TFSI (TEA-TFSI) in acetonitrile at 3 C (Panel (a)) and at 5 C (Panel (b)) cycling rates.

FIG. 7 provides plots of capacity (left vertical axis) and efficiency (right vertical axis) versus cycle number (horizontal axis) for 0.5 M TEMPO-EG1 in 1 M tetraethyl ammonium TFSI (TEA-TFSI) in acetonitrile at 3 C (Panel (a)) and at 5 C (Panel (b)) cycling rates. In FIG. 10, carbon papers were used the electrodes, while the separator was a CELGARD 2325 membrane. The circulation rate of the electrolytes was 20 ml/min. The data in FIG. 6 and FIG. 7 show that using TEATFSI, symmetrical cycling of 0.5 M TEMPO-EG1 was obtained at 3 C and 5 C rates. The discharge capacity faded faster than the cycling shown in FIG. 7, Panel (b), and a lower utilization ratio (about 50%) was observed, implying significant levels of polarization on the electrodes.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All numerical values obtained by measurement (e.g., weight, concentration, physical dimensions, removal rates, flow rates, and the like) are not to be construed as absolutely precise numbers, and should be considered to encompass values within the known limits of the measurement techniques commonly used in the art, regardless of whether or not the term "about" is explicitly stated. All methods described herein can be performed in any suitable order unless otherwise indicated herein or otherwise clearly contradicted by context. The use of any and all examples, or exemplary language (e.g., "such as") provided herein, is intended merely to better illuminate certain aspects of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Embodiments of the invention in which an exclusive property or privilege is claimed are defined as follows:

1. A redox flow battery comprising:
    (a) a cathode within a catholyte chamber;
    (b) a catholyte reservoir in fluid-flow connection with the catholyte chamber;
    (c) an anode within an anolyte chamber;
    (d) an anolyte reservoir in fluid-flow connection with the anolyte chamber;
    (e) a catholyte comprising a first redox reactant within the catholyte reservoir and the catholyte chamber;
    (f) an anolyte comprising a second redox reactant within the anolyte reservoir and the anolyte chamber; and
    (g) an ion-permeable separator membrane forming at least a portion of a common wall between the anolyte chamber and the catholyte chamber;
    wherein:
    the catholyte within the catholyte chamber contacts the cathode and the separator membrane;
    the anolyte within the anolyte chamber contacts the anode and the separator membrane;
    the first redox reactant has a higher redox potential than the second redox reactant;
    and the first redox reactant comprises a compound of Formula (I):

(I)

wherein x is 1, 2, or 3; R' is $C_1$ to $C_4$ alkyl or substituted-alkyl; each R" independently is selected from the group consisting of H, alkyl, substituted-alkyl, and halogen; and each substituted-alkyl independently is alkyl in which at least one hydrogen thereof is substituted by one or more moiety selected from the group consisting of —F, —Cl, —Br, —CN, —$CF_3$, alkenyl, alkynyl, —C(=O)0H, —C=OH, —C(=O)R''', —OR''', —SH, —SR''', —$NH_2$, —NHR''', —NR'''$_2$, —SiR'''$_3$, —OSiR'''$_3$, —S(O)OH, and —P(O)(OH)$_2$; and wherein R''' is alkyl or aryl;

and wherein, during charging and discharging of the redox flow battery, the anolyte and the catholyte are circulated through the anolyte chamber and the catholyte chamber, respectively, while cations from the anolyte and catholyte shuttle through the separator membrane to balance the charges that develop within the anolyte and catholyte due to oxidation and reduction of the first and second redox reactants.

2. The redox flow battery of claim 1, wherein each R" independently is H or Ci to $C_4$ alkyl.

3. The redox flow battery of claim 1, wherein each R" is H.

4. The redox flow battery of claim 1, wherein R' is methyl or ethyl.

5. The redox flow battery of claim 1, wherein at least one of R" is a halogen.

6. The redox flow battery of claim 1, wherein at least one of R" is F.

7. The redox flow battery of claim 1, wherein the compound of Formula (I) is dissolved in a non-aqueous polar organic solvent or an aqueous solvent.

8. The redox flow battery of claim 1, wherein the second redox reactant comprises at least one material selected from the group consisting of a quinoxaline compound, a dipyridyl ketone compound, a viologen compound, a benzophenone compound, an anthraquinone compound, and a redox active metal ion.

9. The redox flow battery of claim 1, wherein the cations comprise one or more cation selected from the group consisting of a hydrogen cation, ammonium cation, an alkali metal ion, an alkaline earth metal ion, a transition metal cation, and an organic cation.

10. The redox flow battery of claim 1, wherein R' is methyl, and each R" is H.

11. An aqueous redox flow battery comprising:
    (a) a cathode within a catholyte chamber;
    (b) a catholyte reservoir in fluid-flow connection with the catholyte chamber;
    (c) an anode within an anolyte chamber;
    (d) an anolyte reservoir in fluid-flow connection with the anolyte chamber;
    (e) a catholyte comprising a first redox reactant dissolved in an aqueous solvent within the catholyte reservoir and the catholyte chamber;
    (f) an anolyte comprising a second redox reactant dissolved in an aqueous solvent within the anolyte reservoir and the anolyte chamber; and
    (g) an ion-permeable separator membrane forming at least a portion of a common wall between the anolyte chamber and the catholyte chamber;
    wherein:
    the catholyte within the catholyte chamber contacts the cathode and the separator membrane;
    the anolyte within the anolyte chamber contacts the anode and the separator membrane;

the first redox reactant has a higher redox potential than the second redox reactant;

and the first redox reactant comprises a compound of Formula (I):

wherein x is an integer from 1 to 8; R' is alkyl or substituted-alkyl; each R" independently is selected from the group consisting of H, alkyl, substituted-alkyl, and halogen; and each substituted-alkyl independently is alkyl in which at least one hydrogen thereof is substituted by one or more moiety selected from the group consisting of —F, —Cl, —Br, —CN, —CF$_3$, alkenyl, alkynyl, —C(=O)OH, —C=OH, —C(=O)R''', —OR''', —SH, —SR''', —NH$_2$, —NHR''', —NR'''$_2$, —SiR'''$_3$, —OSiR'''$_3$, —S(0)OH, and —P(O)(OH)$_2$; and wherein R''' is alkyl or aryl;

and wherein, during charging and discharging of the redox flow battery, the anolyte and the catholyte are circulated through the anolyte chamber and the catholyte chamber, respectively, while cations from the anolyte and catholyte shuttle through the separator membrane to balance the charges that develop within the anolyte and catholyte due to oxidation and reduction of the first and second redox reactants.

12. The aqueous redox flow battery of claim 11, wherein x is 1, 2, or 3, R' is methyl, and each R" is H.

* * * * *

UNITED STATES PATENT AND TRADEMARK OFFICE
CERTIFICATE OF CORRECTION

PATENT NO. : 11,271,237 B2
APPLICATION NO. : 16/524666
DATED : March 8, 2022
INVENTOR(S) : Lu Zhang, Jingjing Zhang and Ilya A. Shkrob It is certified that error appears in the above-identified patent and that said Letters Patent is hereby corrected as shown below:

In the Claims

Claim 1, Column 16, Line 8, delete "-C(=O)0H" and insert -- -C(=O)OH--

Claim 11, Column 18, Line 7, delete "-S(0)OH" and insert -- -S(O)OH--

Signed and Sealed this
Twenty-fourth Day of May, 2022

Katherine Kelly Vidal
*Director of the United States Patent and Trademark Office*